United States Patent
Augello et al.

[11] Patent Number: 5,985,323
[45] Date of Patent: Nov. 16, 1999

[54] MICROCRYSTALLINE CELLULOSE/ ALGINATE WET GRANULATION EXCIPIENT/BINDER

[75] Inventors: Michael Augello, Marlboro; George E. Reier, Somerset, both of N.J.

[73] Assignee: FMC Corporation, Philadelphia, Pa.

[21] Appl. No.: 09/046,359

[22] Filed: Mar. 23, 1998

[51] Int. Cl.⁶ .................... A61K 9/16; A61K 9/20

[52] U.S. Cl. .................. 424/464; 424/465; 424/489; 514/779; 514/781

[58] Field of Search .................... 424/464, 465, 424/489; 514/779, 781

[56] References Cited

U.S. PATENT DOCUMENTS 5,366,742  11/1994  Tuason, Jr. et al. .................. 426/96

*Primary Examiner*—James M. Spear
*Attorney, Agent, or Firm*—Ratner & Prestia; Robert L. Andersen

[57] ABSTRACT

The present invention discloses an improved excipient composition for use as an excipient/binder for wet granulation of pharmaceuticals, a process for preparing the excipient composition, its use in granular pharmaceutical compositions, and compressed pharmaceutical tablets made from the granular pharmaceutical compositions. The excipient composition comprises a dried aqueous slurry of microcrystalline cellulose wetcake and a low viscosity alginate.

8 Claims, No Drawings

MICROCRYSTALLINE CELLULOSE/ALGINATE WET GRANULATION EXCIPIENT/BINDER

The present invention pertains to an improved particulate excipient/binder for wet granulation and tableting of pharmaceuticals. More particularly the invention relates to an excipient composition comprising unattrited microcrystalline cellulose coprocessed with low viscosity sodium alginate, to a process for preparing the excipient composition by drying a slurry of microcrystalline cellulose and the alginate, and to granular pharmaceutical compositions and tablets made therefrom.

BACKGROUND OF THE INVENTION

Microcrystalline cellulose is a purified, partially depolymerized cellulose that is produced by treating a source of cellulose, preferably alpha cellulose in the form of pulp from fibrous plant materials, with a mineral acid, preferably hydrochloric acid. The acid selectively attacks the less ordered regions of the cellulose polymer chain thereby exposing and freeing the crystalline sites which form crystallite aggregates which constitute the microcrystalline cellulose. These are then separated from the reaction mixture, and washed to remove degraded by-products. The resulting wet mass, generally containing 40 to 60 percent moisture, is referred to in the art by several names, including hydrolyzed cellulose, level-off DP cellulose, microcrystalline cellulose, microcrystalline cellulose wetcake or simply wetcake.

When the wetcake is dried and freed of water, the resulting product, microcrystalline cellulose, is a white, odorless, tasteless, relatively free-flowing powder, insoluble in water, organic solvents, dilute alkalis and acids. For a fuller description of microcrystalline cellulose and its manufacture see U.S. Pat. No. 2,978,446. The patent describes its use as a pharmaceutical excipient, particularly as a binder, disintegrant, flow aid, and/or filler for preparation of compressed pharmaceutical tablets. Microcrystalline cellulose is manufactured by FMC Corporation and sold under the designation Avicel® PH cellulose in several grades having average particle sizes ranging from about 20 µm to about 180 µm.

In wet granulations using microcrystalline cellulose, for example Avicel® PH 101, at least one additional ingredient has been required to be used as a binder. Typical binders include corn starch paste, pregelatinized starch, ethyl cellulose, hydroxypropylmethylcellulose, and polyvinylpyrrolidone. Although the corn starch must be dispersed in water to be used in wet granulations, the other binders are often dispersed in water prior to the granulation step to increase their effectiveness. The use of these binders therefore adds additional steps to the granulation process resulting from having to weigh out the individual binders and disperse them in water as needed. An additional consequence is to increase the inventory of excipients. Accordingly there is a need for a single dry, ready-to-use excipient for use in granular and/or tableted pharmaceutical preparations.

U.S. Pat. No. 5,366,742 discloses an aggregate of highly attrited, colloidal microcrystalline cellulose coprocessed with a sodium, calcium alginate complex and use of the resulting aggregate as a readily water dispersible suspending agent for food products such as salad dressings, frozen desserts, dry cocoa mixes and the like. The patent describes the alginate used as a high viscosity sodium alginate which is complexed with calcium to form the sodium, calcium alginate complex.

It has now been found that unattrited microcrystalline cellulose wetcake coprocessed with a low viscosity alginate is more effective as an excipient/binder than prior combinations of microcrystalline cellulose with the binders listed above. This effectiveness is observed in the excellent binding qualities in the granulations and the ease and speed with which they can be prepared. This increased binding effectiveness carries over into the tablets prepared by compressing the granulations, translates into reduced damage to tablets during compression, coating, packaging, and transporting the product to the ultimate user, provides tablets having unexpectedly low friability, and facilitates increased productivity in the manufacturing and handling operations.

These and other advantages and objects of the invention are provided by using as an excipient/binder for pharmaceutical granulations and tableting unattrited microcrystalline cellulose wetcake coprocessed with low viscosity sodium alginate as hereinafter described.

DETAILED DESCRIPTION OF THE INVENTION

In one aspect, the present invention provides an excipient composition for use in wet granulation and tableting of pharmaceutically active ingredients. The excipient composition comprises particles of unattrited microcrystalline cellulose coprocessed with a low viscosity alginate. Coprocessing refers to forming and drying an aqueous slurry of microcrystalline cellulose wetcake and alginate. The excipient composition of this invention may thus be described as a dried aqueous slurry consisting essentially of unattrited microcrystalline cellulose and a low viscosity alginate.

Microcrystalline cellulose useful in the present invention is unattrited microcrystalline cellulose wetcake.

The alginate employed in this invention is preferably low viscosity sodium alginate, but may also be a sodium, calcium salt complex of low viscosity sodium alginate. Thus, the alginate may be selected from the group consisting of low viscosity sodium alginate and a sodium, calcium complex of low viscosity sodium alginate. It is thus important to use an alginate which has a viscosity in the range of about 40 cps to about 80 cps. A suitable product for this purpose is sold by KELCO Div., Monsanto Co. as KELGIN® LV.

If it is desired to use the sodium, calcium salt complex, this salt complex of the low viscosity sodium alginate is preferably formed in situ from low viscosity sodium alginate in the manner and amounts described in U.S. Pat. 5,366,472, which for this purpose is hereby incorporated herein by reference, and/or as shown in example 2 below.

In accordance with the present invention the weight ratio of the microcrystalline cellulose to the alginate is from about 95:5 to about 75:25, preferably from about 95:5 to about 95:15.

In accordance with the process aspect of this invention, the excipient composition described above is suitably prepared by (a) forming an aqueous slurry of unattrited microcrystalline cellulose wetcake, (b) adding the alginate to the stirred slurry, (c) forming a uniform slurry in which the microcrystalline cellulose and alginate are uniformly distributed, (d) drying the uniform slurry, and (e) recovering the particulate composition. The particulate composition resulting from this process is the granulation composition referred to above. It is essentially an agglomerate of the microcrystalline cellulose and alginate which has properties distinct from either of them alone and also distinct from a simple blend of the two.

In yet another aspect of the invention, there is provided a granular pharmaceutical composition comprising the excipient composition described above in admixture with a medicinally effective amount of a pharmaceutically active ingredient. The granular pharmaceutical composition is preferably prepared by blending the excipient composition with a pharmaceutically active ingredient, each in suitable amounts depending on the desired concentration or amount of active ingredient to be included in the final product, then wet granulating and drying the blend in accordance with procedures that are well known to those skilled in the pharmaceutical formulation art.

In carrying out the granulation, however, the water content of the granulated MCC/alginate excipient with an active pharmaceutical agent may need to be controlled for optimum functionality of the excipient/binder. Furthermore, the useful water content will usually vary with each pharmaceutical active agent being granulated. For example, in the case of acetaminophen, the water content of the dried granulation should be in the range of 2–3 weight %, preferably 2–2.75 weight %. When the final formulation is prepared, other components may, and probably will, introduce additional water, raising the final water content to or above 3 weight percent. It is well known that acetaminophen cannot tolerate a water content significantly above 3 weight % because of the hydrolysis that occurs.

It will also be understood by those skilled in the formulation art that various other conventional additives may be included in the granular pharmaceutical composition, such as other binders, diluents, disintegrants, lubricants, flavoring agents, sweetening agents, and the like. Likewise such additional additives may be blended with the resulting pharmaceutical composition as desired prior to tableting. The resulting tableting formulation is then utilized in a conventional manner to prepare compressed tablet formulations of various types, sizes and shapes, as more fully described in the examples set forth below.

The examples set forth below are intended to further illustrate the invention but are not intended to limit the scope of the invention. The examples are designed to show how the coprocessed materials are prepared and how they are used in wet granulations of two representative active agents, acetaminophen and ibuprofen. It will be appreciated by those skilled in the art that many active ingredients may be used, granulated, and tableted in accordance with the present invention. The only envisioned limitation is that the pharmaceutical active must be compatible with the granulation composition in that it does not degrade or adversely react with the excipient composition and is not itself adversely impacted by the excipient composition or other additives employed in the pharmaceutical granulation composition. For example, such actives as analgesics, antipyretics, antibiotics, cough and cold drugs, antiepeteptics, antihistamines, cardiovascular drugs, gastrointestinal drugs, respiratory drugs, vitamins, and combinations of two or more of these and many other classes of drugs may be used in accordance with this invention.

In the examples below, Examples 1 to 3, respectively, show the preparation of a preferred wet granulation excipient, a less preferred excipient, and one which is not effective as a wet granulation excipient. The difference between the materials of Examples 1 and 3 is that the microcrystalline cellulose (MCC) wetcake of Example 3 was attrited prior to being coprocessed with the sodium alginate and that of Example 1 was never attrited. The difference between the materials of Examples 1 and 2 is that the former is coprocessed MCC wetcake and sodium alginate, whereas in Example 2 the sodium alginate was converted to the sodium, calcium alginate complex Examples 4a and 4b provide a direct comparison of the effectiveness of MCC/sodium alginate and MCC/sodium, calcium alginate as excipients in wet granulations of acetaminophen, showing the former to be the more preferred. For comparison, Example 4c details the use of microcrystalline cellulose in combination with a commonly used binder, polyvinylpyrrolidone, in a wet granulation. The resulting tablets in which polyvinylpyrrolidone was the binding agent exhibited significant capping and were greatly inferior to the tablets of either Example 4a or 4b. Examples 5a through 5c show the same trends except that ibuprofen was the active agent that was wet granulated.

Examples 6a through 6d show the effects of several levels of the MCC/sodium alginate excipient in the wet granulation of acetaminophen. The percentages of MCC/sodium alginate excipient in Examples 6a through 6d are 5%, 10%, 15%, and 20% by weight, respectively. Accordingly, a range of 5–20 wt % of the coprocessed MCC/sodium alginate powder is useful in wet granulations, and a preferred range is 8–20 wt %.

Examples 6e and 6f are directly comparable with Example 6b. The differences here are in the raw materials that were coprocessed to prepare the excipient. Example 6b was prepared from low viscosity sodium alginate whereas Example 6e was prepared from high viscosity sodium alginate. The former yields tablets which have much less friability than the latter. Example 6f was made from low viscosity sodium alginate that was coprocessed with attrited, i.e., colloidal, wetcake. The tablets in Example 6f exhibited capping and were not subjected to friability testing because they were clearly inferior.

Example 7 compares a physical blend of MCC with sodium alginate with the coprocessed material of Example 1 and also with a formulation using only MCC without any sodium alginate, neither coprocessed nor blended, being present. The pure MCC formulation (Example 7c) fails because of its unacceptably high friability. Although the blended excipient of MCC and sodium alginate (Example 7a) is a significant improvement over pure MCC, its friability is more than twice that of the coprocessed MCC/sodium alginate binder.

The coprocessed material of Example 1 has a ratio of MCC:sodium alginate of 85:15. In Examples 8a and 8b the ratio of MCC: sodium alginate is 95:5 and 90:10, respectively. The formulation of Example 8a provides excellent properties, better than those of Example 8b. A comparison of these two examples shows that in Example 8b the water content of the final blend was significantly less than that of the final blend in Example 8a. It is well known that acetaminophen tablets usually require about 3 wt % water content for adequate binding. In Example 8b there is insufficient water present to fully activate the binding power of the sodium alginate, although the friability is quite low. Thus, provided that the water content exceeds about 2.5 wt %, these higher ratios of MCC:sodium alginate are useful. At the other end of the range, it is estimated that the ratio of MCC:sodium alginate could be as low as 75:25, although relative costs of the two components would likely dictate the most practical ratio to be used.

EXAMPLE 1

In a 757 liter (200 gallon) vat were placed 68.0 kilograms of wetcake which had not been previously spray dried or attrited and 208.2 liters of water. This mixture was stirred until a smooth slurry had been prepared. To this slurry was added 4.763 kilograms of low viscosity sodium alginate and then mixed, forming a uniform slurry before being homogenized in a single stage at 10,342 kPa (1500 psi). The homogenized slurry was then spray dried using a disk dryer at an inlet temperature of 198.9° C. (385° F.) and an outlet temperature of 106.7° C. (224° F.). The dry powder that was produced had a loose bulk density of 0.43, loss of weight upon drying of 2.0%, and 20% of the particles were larger than 200 mesh (74 microns).

EXAMPLE 2

The procedure of Example 1 was followed except that 45 kilograms of wetcake, 359.6 liters of water, and 3.175 kilograms of low viscosity sodium alginate were used to prepare the slurry. Prior to homogenization, 340 grams of calcium chloride was added to the slurry. The homogenized slurry was then spray dried using a disk dryer at an inlet temperature of 232.2° C. (450° F.) and an outlet temperature of 118.3° C. (245° F.). The dry powder that was produced had a loose bulk density of 0.39, loss of weight upon drying of 1.8%, and 18% of the particles were larger than 200 mesh (74 microns).

EXAMPLE 3

The procedure of Example 1 was followed except that 68 kilograms of colloidal wetcake, 208.2 liters of water, and 5.67 kilograms of low viscosity sodium alginate were used to prepare the slurry. The dry powder that was produced had a loose bulk density of 0.58, loss of weight upon drying of 2.5%, and 7% of the particles were larger than 200 mesh (74 microns).

EXAMPLE 4

In a stainless steel Hobart mixer were placed 3298 grams of acetaminophen and 495 grams of microcrystalline cellulose coprocessed with low viscosity sodium alginate, 85:15, prepared as described in Example 1. These materials were blended for five minutes before 1250 grams of deionized water was slowly added until all powder was incorporated into granular particles. This granulation required 10 minutes after which the granules were dried on a paper-lined tray which was placed in a 60° C. oven for 4 hours and then allowed to remain in the oven overnight. The dried granular material was passed through a # 16 US standard mesh screen and then was placed in a Patterson-Kelley twin shell blender. To this blender were added 178 grams of croscarmellose sodium and 989.5 grams of Avicel® PH 102. These ingredients were mixed for 10 minutes after which 39.5 grams of magnesium stearate which had been passed through a #45 US standard mesh screen was added to the blender. Mixing was continued for an additional 5 minutes. This formulation was compressed on a $B_2$ tablet press using tooling to prepare caplet-shaped tablets. The average weight, thickness, and hardness of these tablets were 0.7556 grams, 5.867 mm (0.2310 inch), and 11.4 Kiloponds, respectively. The disintegration time for these tablets averaged 100 seconds, and their friability was 0.265% after 4 minutes. Dissolution of the active ingredient in 900 mL of 0.05 M phosphate buffer using USP Apparatus 2 equipped with a paddle (USP 23 procedure) was 95% after 30 minutes. This is Example 4a in Table 1. Examples 4b and 4c were prepared in the same manner except that 1750 grams and only 800 grams of deionized water were used in Examples 4b and 4c, respectively.

TABLE 1

| | Example | | |
|---|---|---|---|
| | 4a (grams) | 4b (grams) | 4c (grams) |
| Ingredients | | | |
| Acetaminophen | 3298 | 3298 | 3550 |
| MCC/Na alginate[a] | 495 | | |
| MCC/Na,Ca alginate[b] | | 495 | |
| Polyvinylpyrrolidone[c] | | | 150 |
| Deionized water | 1250 | 1750 | 800 |
| Croscarmellose sodium[d] | 178 | 178 | 193 |
| MCC[e] | 989.5 | 989.5 | 1065.5 |
| Magnesium stearate | 39.5 | 39.5 | 42.5 |
| Tablet Properties | | | |
| Average weight (grams) | 0.7556 | 0.759 | ND[f] |
| Thickness (mm) | 5.8452 | 5.867 | ND |
| Hardness (Kp) | 11.40 | 8.05 | ND |
| Friability[g] (%) | 0.265 | 0.323 | ND |
| Disintegration (seconds) | 100 | 34 | ND |
| Dissolution (%)[h] | 95 | 95 | ND |

[a]Prepared in Example 1
[b]Prepared in Example 2
[c]Polyvinylpyrrolidone 29/32, sold by BASF Corporation
[d]Ac—Di—Sol ®, FMC Corporation, Philadelphia, PA 19103
[e]Avicel ® PH-102, FMC Corporation, Philadelphia, PA 19103
[f]Not measured because "capping off" occurred during tableting, indicating inferior tablets
[g]Friability measurements were made after 4 minutes.
[h]Dissolution measurements were taken after 30 minutes

EXAMPLE 5

In a stainless steel Hobart mixer were placed 3040 grams of ibuprofen and 570 grams of microcrystalline cellulose coprocessed with low viscosity sodium alginate, 85:15, prepared as described in Example 1. These materials were blended for five minutes before 1200 grams of deionized water was slowly added until all powder was incorporated into granular particles. This granulation required 10 minutes after which the granules were dried on a paper-lined tray which was placed in a 50° C. oven for 4 hours and then allowed to remain in the oven overnight. The dried granular material was passed through a # 16 US standard mesh screen and then was placed in a Patterson-Kelley twin shell blender. To this blender were added 205 grams of croscarmellose sodium and 1140 grams of Avicel® PH 102. These ingredients were mixed for 10 minutes after which 45.5 grams of magnesium stearate which had been passed through a #45 US standard mesh screen was added to the blender. Mixing was continued for an additional 5 minutes. This formulation was compressed on a $B_2$ tablet press using tooling to prepare caplet-shaped tablets. The average weight, thickness, and hardness of these tablets were 0.6580 grams, 5.585 mm (0.2199 inch), and 2.81 Kiloponds, respectively. The disintegration time for these tablets averaged 35 seconds, and their friability was 0.30% after 4 minutes. Dissolution of the active ingredient in 900 mL of 0.05 M phosphate buffer using USP Apparatus 2 equipped with a paddle (USP 23 procedure) was 85% after 60 minutes. This is Example 5a in Table 2. Examples 5b and 5c were prepared in the same manner except that only 800 grams of deionized water was used in Example 5c.

TABLE 2

| | Example | | |
|---|---|---|---|
| | 5a (grams) | 5b (grams) | 5c (grams) |
| Ingredients | | | |
| Ibuprofen | 3040 | 3040 | 3311.5 |
| MCC/Na alginate[a] | 570 | | |
| MCC/Na, Ca alginate[b] | | 570 | |
| Polyvinylpyrrolidone[c] | | | 173.5 |
| Deionized water | 1200 | 1200 | 800 |
| Croscarmellose sodium[d] | 205 | 205 | 223.5 |
| MCC[e] | 1140 | 1140 | 1241.5 |
| Magnesium stearate | 45.5 | 45.5 | 45.0 |
| Tablet Properties | | | |
| Average weight (grams) | 0.658 | 0.657 | 0.593 |
| Thickness (mm) | 5.585 | 5.624 | 5.126 |
| Hardness (Kp) | 2.81 | 2.03 | 6.84 |
| Friability (%) | 0.30 | 0.41 | ND[g] |
| Disintegration (seconds) | 35 | 52 | 75 |
| Dissolution (%)[h] | 85 | 87 | ND[i] |

[a]Prepared in Example 1
[b]Prepared in Example 2
[c]Polyvinylpyrrolidone 29/32, sold by BASF Corporation
[d]Ac—Di—Sol ®, FMC Corporation, Philadelphia, PA 19103
[e]Avicel ® PH-102, FMC Corporation, Philadelphia, PA 19103
[f]Friability measurements were made after 4 minutes
[g]Breakage of the tablets occurred in less than 3 minutes
[h]Dissolution measurements were determined after 60 minutes
[i]Not measured

EXAMPLE 6

In a stainless steel Hobart mixer were placed 2095 grams of acetaminophen and 168 grams of microcrystalline cellulose coprocessed with low viscosity sodium alginate, 85:15, prepared as described in Example 1. These materials were blended for five minutes before approximately 800 grams of deionized water was slowly added until all powder was incorporated into granular particles. The granules were dried on a paper-lined tray which was placed in a 60° C. oven for 3.5 hours. The dried granular material was milled through a 0.9 mm Co-mill screen and then was placed in a Patterson-Kelley twin shell blender. To this blender were added 84 grams of croscarmellose sodium and 630 grams of Avicel® PH 102. These ingredients were mixed for 10 minutes after which 25.2 grams of magnesium stearate which had been passed through a #30 US standard mesh screen was added to the blender. Mixing was continued for an additional 5 minutes. This formulation was compressed on a rotary tablet press (Model 512) using tooling to prepare caplet-shaped tablets. The average weight, thickness, and hardness of these tablets were 0.6162 grams, 6.340 mm (0.2496 inch), and 7.89 Kiloponds, respectively. The disintegration time for these tablets averaged less than 5 minutes, and their friability was 0.53% after 4 minutes. Dissolution of the active ingredient in 900 mL of 0.05 M phosphate buffer using USP Apparatus 2 equipped with a paddle (USP 23 procedure) was 87% after 30 minutes. This is Example 6a in Table 3. Examples 6b, 6c, and 6d were prepared in the same manner.

TABLE 3

| | Example | | | |
|---|---|---|---|---|
| | 6a (grams) | 6b (grams) | 6c (grams) | 6d (grams) |
| Ingredients | | | | |
| Acetaminophen | 2095 | 1997 | 1873 | 1712 |
| MCC/Na alginate[a] | 168 | 300 | 467 | 685 |
| Deionized water | 899 | 800 | 800 | 800 |
| Croscarmellose sodium[b] | 84 | 79.8 | 75 | 69 |
| MCC[c] | 630 | 599 | 562 | 513.6 |
| Magnesium stearate | 25.2 | 23.9 | 22.5 | 20.6 |
| Tablet Properties | | | | |
| Average weight (grams) | 0.616 | 0.611 | 0.622 | 0.631 |
| Thickness (mm) | 6.340 | 6.309 | 6.398 | 6.459 |
| Hardness (Kp) | 7.89 | 8.68 | 5.42 | 5.34 |
| Friability[d] (%) | 0.53 | 0.253 | 0.485 | 0.34 |
| Disintegration (minutes) | <5 | <15 | >15 | >15 |
| Dissolution (%)[e] | 87 | 89 | 91 | NM[f] |

[a]Prepared in Example 1
[b]Ac—Di—Sol ®, FMC Corporation, Philadelphia, PA 19103
[c]Avicel ® PH-102, FMC Corporation, Philadelphia, PA 19103
[d]Friability measurements were made after 4 minutes
[e]Dissolution measurements were determined after 30 minutes
[f]Not measured Additional formulations were prepared using other coprocessed microcrystalline cellulose and sodium alginate materials following the identical procedure of Example 6a using the formulation of Example 6b. These are identified as 6e and 6f and are compared in Table 4 with Example 6b.

TABLE 4

| | Example | | |
|---|---|---|---|
| | 6b (grams) | 6e (grams) | 6f (grams) |
| Ingredients | | | |
| Acetaminophen | 1997 | 1997 | 1997 |
| MCC/Na alginate | 300[a] | 300[b] | 300[c] |
| Deionized water | 800 | 800 | 800 |
| Croscarmellose sodium[d] | 79.8 | 79.8 | 79.8 |
| MCC[e] | 599 | 599 | 599 |
| Magnesium stearate | 23.9 | 23.9 | 23.9 |
| Tablet Properties | | | |
| Average weight (grams) | 0.611 | 0.647 | 0.710 |
| Thickness (mm) | 6.309 | 6.662 | 7.328 |
| Hardness (Kp) | 8.68 | 9.87 | 9.53 |
| Friability[f] (%) | 0.253 | 0.456 | ND[g] |
| Disintegration (minutes) | <15 | >15 | ND |
| Dissolution (%)[h] | 89 | ND | ND |

[a]Prepared in Example 1
[b]Prepared as in Example 1 by substituting high viscosity sodium alginate for low viscosity sodium alginate
[c]Prepared in Example 3
[d]AC—Di—SOl ®, FMC Corporation, Philadelphia, PA 19103
[e]Avicel ® PH-102, FMC Corporation, Philadelphia, PA 19103
[f]Friability measurements were made after 4 minutes
[g]Not measured
[h]Dissolution measurements were determined after 30 minutes

EXAMPLE 7

In a stainless steel Hobart mixer were placed 3360 grams of acetaminophen, 400 grams of microcrystalline cellulose (Avicel® PH-101), and 80 grams of low viscosity sodium alginate. These materials were blended for five minutes before approximately 1250 grams of deionized water was slowly added until all powder was incorporated into granular particles. The granules were dried on a paper-lined tray which was placed in a 60° C. oven for 3.5 hours. The dried granular material was milled through a 0.9 mm Co-mill screen and then was placed in a Patterson-Kelley twin shell blender. To this blender was added 120 grams of croscarmellose sodium (Ac-Di-Sol). These ingredients were mixed for 10 minutes after which 40 grams of magnesium stearate which had been passed through a #30 US standard mesh screen was added to the blender. Mixing was continued for an additional 5 minutes. This formulation was compressed on a rotary tablet press (Model 512) using tooling to prepare caplet-shaped tablets. The average weight, thickness, and hardness of these tablets were 0.592 grams, 6.223 mm (0.245 inch), and 11.1 Kiloponds, respectively. The disintegration time for these tablets averaged 782 seconds, and their friability was 1.38% after 4 minutes with capping of the tablets. This is Example 7a in Table 5. Examples 7b, and 7c were prepared in the same manner using different granulating agents. The compositions of these caplets and the results are summarized in Table 5.

TABLE 5

| | Example | | |
|---|---|---|---|
| | 7a (grams) | 7b (grams) | 7c (grams) |
| Ingredients | | | |
| Acetaminophen | 3360 | 3338.8 | 3338.8 |
| MCC[a] | 400 | — | 500.8 |
| Sodium alginate | 80 | — | — |
| MCC/Na alginate[b] | — | 500.8 | — |
| Deionized water | 1250 | 1250 | 1350 |
| Croscarmellose sodium[c] | 120 | 120 | 120 |
| Magnesium stearate | 40 | 40 | 40 |
| Tablet Properties | | | |
| Average weight (grams) | 0.592 | 0.591 | 0.594 |
| Thickness (mm) | 6.223 | 6.096 | 6.231 |
| Hardness (Kp) | 11.1 | 10.89 | 5.53 |
| Friability[d] (%) | 1.38 | 0.52 | 5.97 |
| Disintegration (seconds) | 782 | 666 | 77 |

[a] Avicel ® PH-101, FMC Corporation, Philadelphia, PA 19103
[b] Prepared in Example 1
[c] Ac—Di—Sol ®, FMC Corporation, Philadelphia, PA 19103
[d] Friability measurements were made after 4 minutes

EXAMPLE 8

On a vertical granulator (Model FMVG-25, Powrex Corporation) were placed 3457.5 grams of acetaminophen and 495 grams of microcrystalline cellulose coprocessed with low viscosity sodium alginate, 95:5, prepared by the method described in Example 1. The blade of the granulator was operated at 603 rpm and the chopper at 1592 rpm. These materials were blended for five minutes before approximately 1250 grams of deionized water was sprayed into the granulator at a rate of 155 grams/minute. The addition of water required 7 minutes and was followed by continued granulation for five minutes. The granules were dried on a paper-lined tray which was placed in a 60° C. oven for 2.5 hours. The dried granular material was passed through a #16–18 mesh screen and then was placed in a Patterson-Kelley twin shell blender. To this blender were added 187 grams of croscarmellose sodium (Ac-Di-Sol, FMC Corporation, Philadelphia, Pa. 19103) and 1037.5 grams of Avicel® PH 102 (FMC Corporation, Philadelphia, Pa. 191003). These ingredients were mixed for 10 minutes after which 41.2 grams of magnesium stearate which had been passed through a #30 US standard mesh screen was added to the blender. Mixing was continued for an additional 5 minutes. This formulation was compressed on a rotary tablet press (Model 512) using tooling to prepare caplet-shaped tablets. The average weight, thickness, and hardness of these tablets were 0.765 gram, 5.751 mm (0.2264 inch), and 9.43 Kiloponds, respectively. The disintegration time for these tablets averaged less than 3 minutes, and their friability was 0.32% after 4 minutes. This is Example 8a.

The procedure of Example 8a was followed exactly, substituting as the binder microcrystalline cellulose coprocessed with low viscosity sodium alginate (90:10) prepared by the method of Example 1. The wet granulation of this material and acetaminophen after drying had a water content of 1.352 wt %, and the water content of the final mixture prior to compression was 2.332 wt %. The weight, thickness, and hardness of these tablets were almost identical to those prepared in Example 8a, and their friability was 0.387%. This is Example 8b.

What is claimed:

1. An excipient composition comprising particles of a dried aqueous slurry consisting essentially of unattrited microcrystalline cellulose wetcake and a low viscosity alginate selected from the group consisting of low viscosity sodium alginate and a sodium, calcium salt complex of low viscosity sodium alginate in which the low viscosity alginate has a viscosity in the range of 40 to 80 cps.

2. The composition of claim 1 in which the alginate is low viscosity sodium alginate.

3. A process for preparing the composition of claim 1 comprising the steps of (a) forming an aqueous slurry of undried unattrited microcrystalline cellulose wetcake, (b) adding the alginate to the stirred slurry (c) forming a uniform slurry in which the microcrystalline cellulose and alginate are uniformly distributed, (d) drying the uniform slurry and (e) recovering the a particulate composition.

4. The composition of claim 1 in which the weight ratio of microcrystalline cellulose to alginate is from 95:5 to 75:25.

5. The composition of claim 1 in which the weight ratio of microcrystalline cellulose to alginate is from 95:5 to 85:15.

6. The composition of claim 1 in which the alginate is low viscosity sodium alginate having a viscosity in the range of 40 to 80 cps and the weight ratio of microcrystalline cellulose to alginate is in the range of 95:5 to 85:15.

7. A granular pharmaceutical composition comprising the granulation composition of any of claims 1, 2, 4, 5 or 6 in admixture with a medicinally effective amount of a pharmaceutically active ingredient.

8. A compressed pharmaceutical tablet comprising the pharmaceutical composition of claim 7 admixture with a pharmaceutically acceptable compatible binder, diluent, disintegrant, flavoring agent, lubricant or mixture thereof.

* * * * *